(12) United States Patent
Litvin et al.

(10) Patent No.: US 9,390,523 B2
(45) Date of Patent: Jul. 12, 2016

(54) DETERMINATION OF Z-EFFECTIVE VALUE FOR SET OF VOXELS USING CT DENSITY IMAGE AND SPARSE MULTI-ENERGY DATA

(75) Inventors: Andrew Litvin, Stoneham, MA (US); Ram Naidu, Newton, MA (US); David Lieblich, Worcester, MA (US); Sergey Simanovsky, Brookline, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 72 days.

(21) Appl. No.: 14/397,751

(22) PCT Filed: May 1, 2012

(86) PCT No.: PCT/US2012/035984
§ 371 (c)(1),
(2), (4) Date: Oct. 29, 2014

(87) PCT Pub. No.: WO2013/165396
PCT Pub. Date: Nov. 7, 2013

(65) Prior Publication Data
US 2015/0104089 A1   Apr. 16, 2015

(51) Int. Cl.
*G06T 11/00* (2006.01)
*G01N 23/04* (2006.01)

(52) U.S. Cl.
CPC ............ G06T 11/006 (2013.01); G01N 23/046 (2013.01); *G06T 2211/408* (2013.01); *G06T 2211/424* (2013.01); *G06T 2211/436* (2013.01)

(58) Field of Classification Search
None
See application file for complete search history.

(56) References Cited

U.S. PATENT DOCUMENTS 7,190,757 B2 *   3/2007   Ying ................... G01N 23/046
                                                            378/5

OTHER PUBLICATIONS

Maab, Clemens. "Exact Dual Energy Material Decomposition from Inconsistent Rays." Medical Physics 38, No. 2 (Feb. 2011): 691-700. Accessed Feb. 21, 2016. http://scitation.aip.org/content/aapm/journal/medphys/38/2/10.1118/1.3533686.*

(Continued)

*Primary Examiner* — Utpal Shah
*Assistant Examiner* — Kate R Duffy
(74) *Attorney, Agent, or Firm* — Cooper Legal Group, LLC (57) ABSTRACT

Z-effective (e.g., atomic number) values are generated for one or more sets of voxels in a CT density image using sparse (measured) multi-energy projection data. Voxels in the CT density image are assigned a starting z-effective value, causing a CT z-effective image to be generated from the CT density image. The accuracy of the assigned z-effective values is tested by forward projecting the CT z-effective image to generate synthetic multi-energy projection data and comparing the synthetic multi-energy projection data to the sparse multi-energy projection data. When the measure of similarity between the synthetic data and the sparse data is low, the z-effective value assigned to one or more voxels is modified until the measure of similarity is above a specified threshold (e.g., with an associated confidence score), at which point the z-effective values substantially reflect the z-effective values that would be obtained using a (more expensive) dual-energy CT imaging modality.

20 Claims, 7 Drawing Sheets

(56) References Cited

OTHER PUBLICATIONS

International Search Report cited in related application No. PCT/US2012/035984 dated Sep. 10, 2012, pp. 10.

Maass, et al., "Exact dual energy material decomposition from inconsistent rays (MDIR)", Medi Cal Physics, AIP, Melville, NY, US, vol. 38, No. 2, Jan. 11, 2011, pp. 691-700, XP012145072, ISSN: 0094-2405, 001: 10.1118/1.3533686 abstract; figures 1,5 p. 692, right-hand column—p. 695, 1 eft-hand column sec. II, IIMethod II, I 1-8, "Polychromatic forward proj ect ion", II -D, "MDIR".

* cited by examiner

DETERMINATION OF Z-EFFECTIVE VALUE FOR SET OF VOXELS USING CT DENSITY IMAGE AND SPARSE MULTI-ENERGY DATA

BACKGROUND

The present application relates to the field of imaging, and in particular imaging modalities that produce images utilizing radiation technology (e.g., at times referred to herein as radiography imaging modalities). It finds particular application with medical, security, and/or other applications where obtaining information about physical properties (e.g., density and/or effective atomic number, etc.) of an object under examination may be useful.

CT and other radiography imaging modalities (e.g., single-photon emission computed tomography (SPECT), mammography, digital radiography, etc.) are useful to provide information, or images, of interior aspects of an object under examination. Generally, the object is exposed to radiation photons (e.g., such as X-rays, gamma rays, etc.), and an image(s) is formed based upon the radiation absorbed and/or attenuated by the interior aspects of the object, or rather an amount of photons that is able to pass through the object. Traditionally, the image(s) that is formed from the radiation exposure is a density image or attenuation image, meaning the image is colored/shaded as a function of the respective densities of sub-objects comprised within the object under examination. For example, highly dense sub-objects absorb and/or attenuate more radiation than less dense sub-objects, and thus a sub-object having a higher density, such as a bone or metal, for example, will be shaded differently than less dense sub-objects, such as muscle or clothing.

While such imaging systems have proven successful, in some applications imaging based upon more than density may be advantageous. For example, in security applications, certain threat items can be hidden amongst clothing or other non-threat items that have similar densities to the threat items. Thus, in some applications, such as airport security, it may be useful to determine other and/or additional physical properties of the item under examination, such as, for example, effective atomic number (e.g., at times also referred to as z-effective). In this way, threat items that have densities similar to non-threat items, but different atomic numbers, for example, can be more correctly identified.

As early as 1992, multi-energy imaging modalities have been deployed in some environments, such as airport and military establishments, to provide additional information about an object under examination, such as an object's effective atomic number(s). These modalities have provided improved detection and false alarm performance when tasked to differentiate between sub-objects, relative to systems that merely differentiate sub-objects based upon density.

Multi-energy imaging modalities operate by using multiple, distinct radiation photon energy spectra to reconstruct an image(s) of an object. Such distinct energy spectra can be measured using numerous techniques. For example, multi-energy measurements can be performed using energy resolving detectors (e.g., where the detectors are configured to selectively detect radiation having an energy within a first energy spectrum from radiation having an energy within a second energy spectrum), two radiation sources (e.g., respectively emitting radiation at a different energy level/spectrum), and/or by varying the voltage applied to a radiation source (e.g., such that the energy of emitted radiation varies as the applied voltage varies).

Two widely-used multi-energy imaging modalities are a dual-energy CT scanner and a dual-energy line scanner (e.g., also referred to as a dual-energy projection scanner). While both have proven effective, respective scanners have drawbacks. For example, dual-energy CT scanners are costly to produce because they generally require detectors that are more costly to manufacture than detectors used on single-energy scanners and/or require one or more high voltage sources that can rapidly modulate the power supplied to a radiation source(s). Dual-energy line scanners, while less expensive to manufacture than dual-energy CT scanners, generally have a higher false alarm rate than dual-energy CT scanners (and thus may be unable to pass security certifications) because dual-energy line scanners typically yield data from, at most, a few views, for example. Thus, the more sub-objects within an object (e.g., the more densely compacted items are in a suitcase), the more difficult it is for a dual-energy line scanner (e.g., which generally merely generates a top-down image) to discriminate between the density and/or atomic number of a first item and a second item if the items are stacked on top of one another, for example. Stated differently, the more crowded the suitcase, the less likely it is that a dual-energy line scanner will have a clear line integral measurement from which to derive a z-effective for a particular sub-object of interest.

SUMMARY

Aspects of the present application address the above matters, and others. According to one aspect, a method for generating a z-effective value for a set of voxels in a CT density image for a radiography imaging modality is provided. The method comprises acquiring the CT density image of an object and acquiring sparse multi-energy projection data of the object. The method also comprises identifying one or more sets of voxels in the CT density image and setting an initial z-effective value for respective sets of voxels to generate a CT z-effective image. The method further comprises forward projecting the CT z-effective image to generate synthetic multi-energy projection data and comparing the synthetic multi-energy projection data to the sparse multi-energy projection data to determine a measure of similarity between z-effective information of the synthetic multi-energy projection data and the z-effective information of the sparse multi-energy projection data. The method also comprises updating the initial z-effective value for one or more sets of voxels to update the CT z-effective image when the determined measure of similarity between the z-effective information of the synthetic multi-energy projection data and the z-effective information of the sparse multi-energy projection data is below a specified threshold.

According to another aspect, a system for generating a z-effective value for a set of voxels in a CT density image is provided. The system comprises a segmentation component configured to segment one or more sub-objects from the CT density image of an object under examination and a z-effective component configured to set a first z-effective value for a first set of voxels representing a first segmented sub-object in the CT density image and a second z-effective value for a second set of voxels representing a second segmented sub-object in the CT density image to generate a CT z-effective image. The system also comprises a forward projection component configured to forward project the CT z-effective image to generate synthetic multi-energy projection data and a comparison component configured to compare the synthetic multi-energy projection data to sparse multi-energy projection data indicative of the object to determine a measure of similarity between z-effective information of the synthetic multi-energy projection data and z-effective information of the sparse multi-energy projection data. A measure of similarity that is below a specified threshold is indicative of at least one of the first z-effective value and the second z-effective value differing from an atomic number of a sub-object represented thereby by at least a specified deviation.

According to yet another aspect, a computer-readable storage medium comprising computer executable instructions that when executed via a processor perform a method is provided. The method comprises setting an initial z-effective value for respective voxels of a CT density image acquired from a single-energy radiography examination of an object to generate a CT z-effective image and forwarding projecting the CT z-effective image to generate synthetic multi-energy projection data. The method also comprises comparing the synthetic multi-energy projection data to sparse multi-energy projection data indicative of the object to determine a measure of similarity between z-effective information of the synthetic multi-energy projection data and z-effective information of the sparse multi-energy projection data.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are described herein for generating at least one z-effective value for a set of voxels using a CT density image and sparse multi-energy projection data. Such a CT density image may be acquired from a reconstruction of CT data and/or other data, and the sparse multi-energy projection data be acquired by sparsely populating the CT detector array with energy resolving elements and/or using a separate multi-energy imaging modality (such as a dual-energy line scanner). As will be described in more detail below, the z-effective value(s) for a set of voxels is (are) derived based upon an iterative approach whereby estimated z-effective values for one or more sets of voxels in the CT density image of the object are refined until synthetic multi-energy projection data generated therefrom substantially matches the sparse (measured) multi-energy projection data, representative of the object under examination.

It will be appreciated that "sparse multi-energy projection data" and/or the like is intended to refer to measured multi-energy projection data acquired from sparsely arranged energy resolving elements of a CT detector array and/or from a separate multi-energy imaging modality. By comparison, "synthetic multi-energy projection data" is generated from estimated z-effective values for one or more sets of voxels in a CT density image. Thus, whereas the sparse multi-energy projection data reflects measurements made during an examination of an object, the synthetic multi-energy projection data reflects estimates made during an iterative process (e.g., which, as will be described below, can be compared to the sparse multi-energy projection data to determine the accuracy of the estimates).

It will be appreciated that "sparse multi-energy projection data" and/or the like is intended to describe how the data is insufficient/inadequate to be reconstructed into a full resolution image. That is, the sparse multi-energy projection data generally cannot be reconstructed to form a z-effective image (e.g., where the z-effective for respective voxels is determined independently). For example, while the sparse multi-energy projection data can be acquired from a CT scanner, the sparsity of energy resolving detectors within the detector array does not generally allow a 3D image of sufficient resolution and accuracy to be generated solely from the output of the energy resolving detectors. Thus, while there may be some multi-energy data points of reference, images generated from data output by the CT scanner are typically merely CT density images. Similarly, data produced by a multi-energy line scanner is typically not sufficient to reconstruct a z-effective image of sufficient resolution and accuracy because the object is viewed from a limited number of angles.

Figure 1:
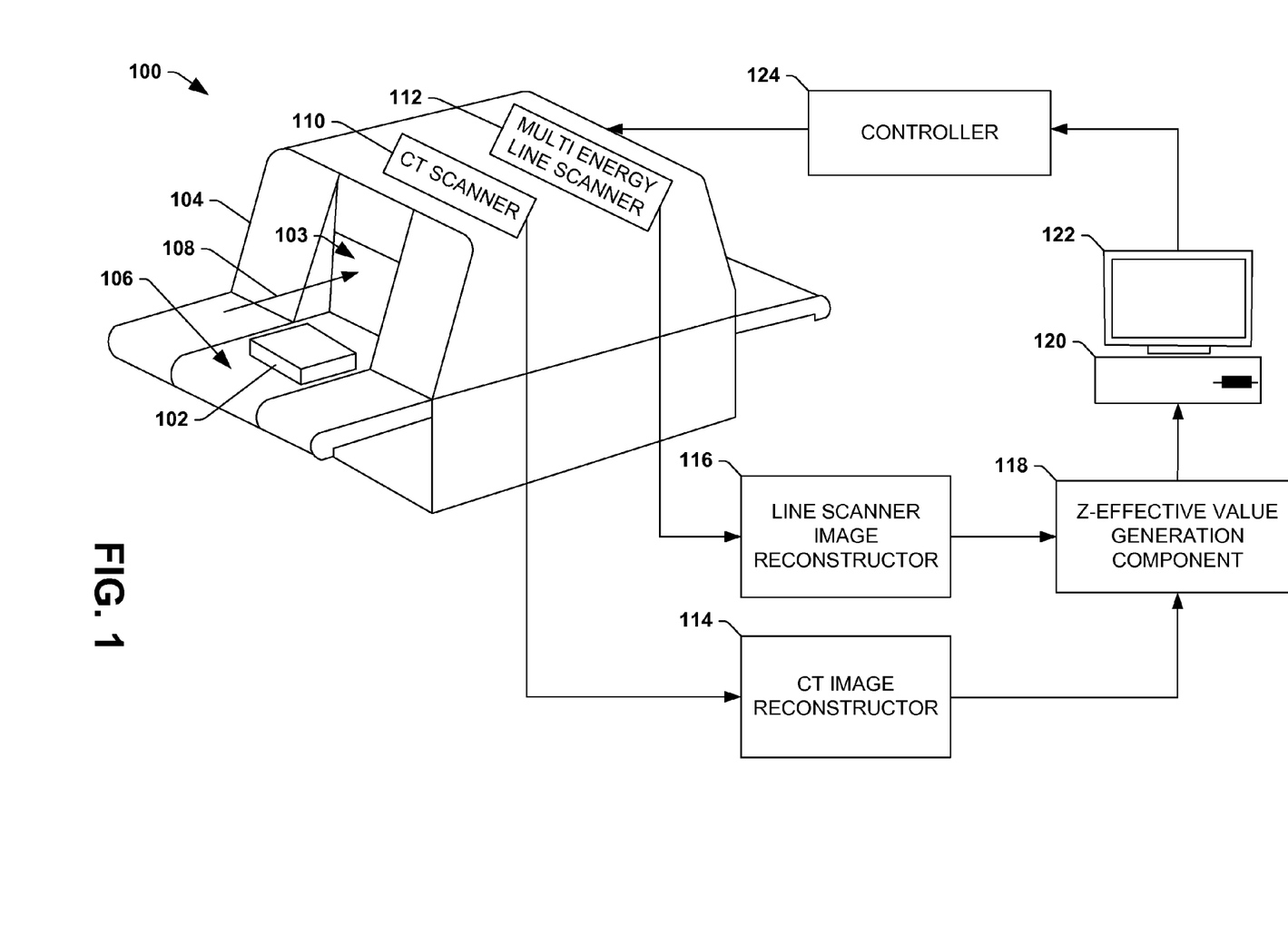
FIG. 1 is a schematic block diagram illustrating an example examination environment for examining an object.

FIG. 1 illustrates an example environment 100 for generating z-effective values for a set of voxels using a CT density image (e.g., which may be an image slice (e.g., a 2D image), a collection of slices, and/or a 3D image) and sparse multi-energy projection data. More particularly, FIG. 1 illustrates an example object examination apparatus 104 comprising a CT scanner 110 (e.g., a first imaging modality) and a multi-energy line scanner 112 (e.g., a second imaging modality). Respective imaging modalities are configured to examine an object 102 (e.g., suitcase, animal, human, etc.) and generate data based upon the examination that can be utilized, in combination, to generate at least one z-effective value for a set of voxels representative of the object 102 and/or sub-objects thereof. For example, the CT scanner 110 may be configured to produce data from which a CT density image may be derived and the multi-energy line scanner may be configured to produce sparse multi-energy projection data.

As illustrated herein, an object 102 (e.g., suitcase, human, etc.) to be examined is placed on an object support 106 and positioned in the object examination apparatus 104 through an opening or bore 103 of the object examination apparatus 104. For example, in the illustrated embodiment, the object support 106 is a conveyor belt configured to convey 108 the object 102 into an examination region of the object examination apparatus 104, where it can be examined using the CT scanner 110 and the multi-energy line scanner 112.

The CT scanner 110 and the multi-energy line scanner 112 are configured to respectively examine the object 102 using radiation (e.g., X-rays, gamma rays, etc.). Typically, the CT scanner 110 is configured to rotate a radiation source and/or detector array about the object 102 during the examination, causing the object 102 to be viewed and/or illuminated from a plurality of angles (e.g., where the position of the radiation source and/or detector array are changed relative to the object). In this way, the CT scanner 110 may generate volumetric data indicative of the object 102 from which a CT density image(s) (e.g., representative of a 3D volume, a collection of 2D slices of an object and/or a single 2D slice) may be derived. Conversely, the multi-energy line scanner 112 is generally configured to view and/or illuminate the object 102 from a limited number of angles (e.g., typically one or two angles). Thus, a single two-dimensional or projection image(s) of the object 102 is typically generated from the data produced by the multi-energy line scanner 112, as opposed to the typically hundreds of projections generated by a CT (e.g., from which the CT density image is derived), for example.

In the example environment 100, the CT scanner 110 may be a single-energy scanner (e.g., not configured to distinguish radiation photons based upon their respective energies) because the sparse multi-energy projection data may be acquired from the multi-energy line scanner 112, which is configured to utilize one or more techniques for capturing multi-energy measurements of the object 102. By way of example, the multi-energy line scanner 112 may comprise two or more radiation sources respectively configured to emit radiation at a different energy level/spectrum, may comprise merely one radiation source configured to emit radiation at two or more distinct energy spectra (e.g., by varying a voltage applied to the source), and/or may comprise energy resolving detectors configured to distinguish radiation having a first energy spectrum from radiation having a second energy spectrum.

In the illustrated environment 100, data output by the CT scanner 110 may be transmitted to a CT image reconstructor 114 configured to generate one or more CT density images representative of the object 102 under examination using analytical, iterative, and/or other image reconstruction techniques (e.g., backprojection, tomosynthesis reconstruction, iterative reconstruction, etc.). Similarly, data output by the multi-energy line scanner 112 may be transmitted to a line scanner image reconstructor 116 configured to generate one or more multi-energy projection images, for example, representative of the object 102 under examination using analytical, iterative, or other techniques (e.g., backprojection) for generating images from such data.

The example environment 100 further comprises a z-effective value generation component 118 configured to generate a z-effective value for one or more set of voxels respectively corresponding to a sub-object comprised within the object 102 (e.g., where a set of voxels may comprise one or more voxels). More particularly, as will be described in more detailing below, the z-effective value generation component 118 is configured to derive a respective z-effective value for voxels comprised in the CT density image based upon the sparse multi-energy projection data (e.g., yielded from the multi-energy line scanner 112). Stated differently, the z-effective value generation component 118 is configured to utilize an iterative process whereby the z-effective of one or more sub-objects of the object 102, as represented in the CT density image, is estimated/derived using the CT density image and the sparse multi-energy projection data.

The example environment 100 also includes a terminal 120, or workstation (e.g., a computer), configured to receive data from the z-effective value generation component 118, which can be displayed on a monitor 122 to a user (e.g., security personnel, medical personnel, etc.) in textual, graphical, or other human readable form, for example. In one embodiment, z-effective values for a set of voxels can be displayed in different colors. In this way, the user can inspect the image(s) to identify areas of interest within the object(s) 102. The terminal 120 can also be configured to receive user input which can direct operations of the object examination apparatus 104 (e.g., a speed of gantry rotation, an energy level of the radiation, etc.).

In the example environment 100, a controller 124 is operably coupled to the terminal 120. In one example, the controller 124 is configured to receive user input from the terminal 120 and generate instructions for the object examination apparatus 104 indicative of operations to be performed.

It will be appreciated that the example environment 100 merely illustrates one example system for generating the CT density image and the sparse multi-energy projection data. It is not intended to be interpreted as limiting the scope of the disclosure, including the scope of the claims. For example, in another embodiment, the object examination apparatus 104 may be merely comprised of a CT scanner 110. In such an embodiment, the CT scanner 110 may be comprised of a detector array having single-energy detectors and some, sparsely arranged/intermingled, energy resolving detectors, for example (e.g., as further illustrated in FIG. 3). Moreover, in yet another embodiment, the multi-energy line scanner 112 may be substituted with another type of multi-energy imaging modality configured to generate sparse multi-energy projection data, for example.

It will also be appreciated that the illustrated arrangement of the CT scanner 110 and the multi-energy line scanner 112 is merely an example arrangement. In another embodiment, the object 102 may be examined by the multi-energy line scanner 112 before the CT scanner 110. Moreover, in yet another embodiment, the CT scanner 110 and the multi-energy line scanner 112 may be selectively decoupled from one another. Thus, the imaging modalities may not necessarily be part of a single object examination apparatus 104, for example, but rather may be positioned adjacent one another (e.g., where an object is passed from a stand-alone CT scanner to a stand-alone multi-energy line scanner).

Figure 2:
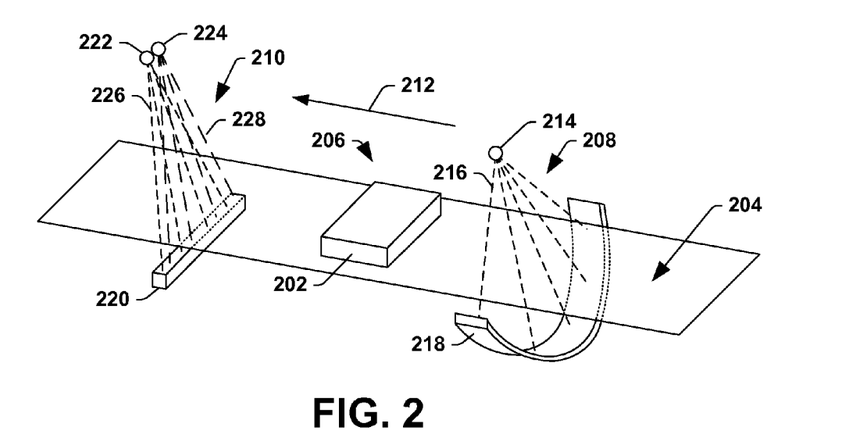
FIG. 2 is a schematic block diagram illustrating an internal view of an example examination environment for examination of an object.

FIG. 2 illustrates an internal view of an object examination apparatus 200 (e.g., 104 in FIG. 1). More particularly, FIG. 2 illustrates an object 202 (e.g., 102 in FIG. 1) being supported on an object support 204 (e.g., 106 in FIG. 1). The object 202 resides in an examination region 206 of the object scanning apparatus 200 (e.g., a region extending from an outside edge of a CT scanner 208 (e.g., 110 in FIG. 1) to an outside edge of a multi energy line scanner 210 (e.g., 112 in FIG. 1)). As illustrated by the arrow 212 (e.g., 108 in FIG. 1), the object 202 is moving from right to left through the examination region 206.

The CT scanner 208, which as described above may be a single-energy CT scanner, comprises, among other things, a radiation source 214 configured to emit radiation 216 and a detector array 218 configured to detect the emitted radiation 216. It will be appreciated that the detector array 218 may be shaped differently than the illustrated arcuate shape. For example, in some embodiments, the detector array 218 may be rectangular. It will also be appreciated that the example CT scanner 208 merely illustrates some of the many components comprised in a CT scanner. Other components of a CT scanner, such as the data acquisition system (DAS), structural support, etc., are not described herein but are nevertheless contemplated as being including in the CT scanner 208.

The radiation source 214 and the detector array 218 are generally mounted on opposite sides of a rotating gantry (not shown) configured to rotate about the object 202 under examination. In this way, the object 202 may be viewed and/or illuminated from a plurality of angles. However, other configurations for viewing the object 202 from a plurality of angles (e.g., to acquire volumetric data) are contemplated herein. For example, in another embodiment, the radiation source 214 and/or detector array 218 may be substantially stationary, and the object 202 may rotate within the examination region 206. In yet another embodiment, the radiation source 214 and/or detector array 218 may be substantially stationary, but the focal spot of the radiation source 214 (an area of the radiation source 214 emitting the radiation) may be moving within a source housing so that the object 202 may be viewed and/or illuminated from a plurality of angles.

The multi-energy line scanner 210 is configured to produce multi-energy projection data from which z-effective information (e.g., atomic number information) can be derived. To do this, the example multi-energy line scanner 210 comprises two radiation sources 222 and 224 and at least one detector array 220. The first source 222 is configured to emit radiation 226 having a first energy level/spectrum, and the second source 224 is configured to emit radiation 228 having a second energy level/spectrum. In this way, radiation having at least two different energy spectra can be detected to generate data that can be used to perform a multi-energy (e.g., dual-energy) decomposition process.

It will be appreciated that other techniques for generating the requisite data to perform multi-energy decomposition are contemplated herein. For example, instead of emitting radiation from two or more sources, the energy level of radiation emitted from a single source may be varied by varying the voltage applied to the source, for example. In yet another embodiment, the detector array 220 of the multi-energy line scanner 210 may comprise energy resolving detectors configured to differentiate radiation having an energy that falls within a first energy spectrum from radiation having an energy that falls within a second energy spectrum, for example.

Figure 3:
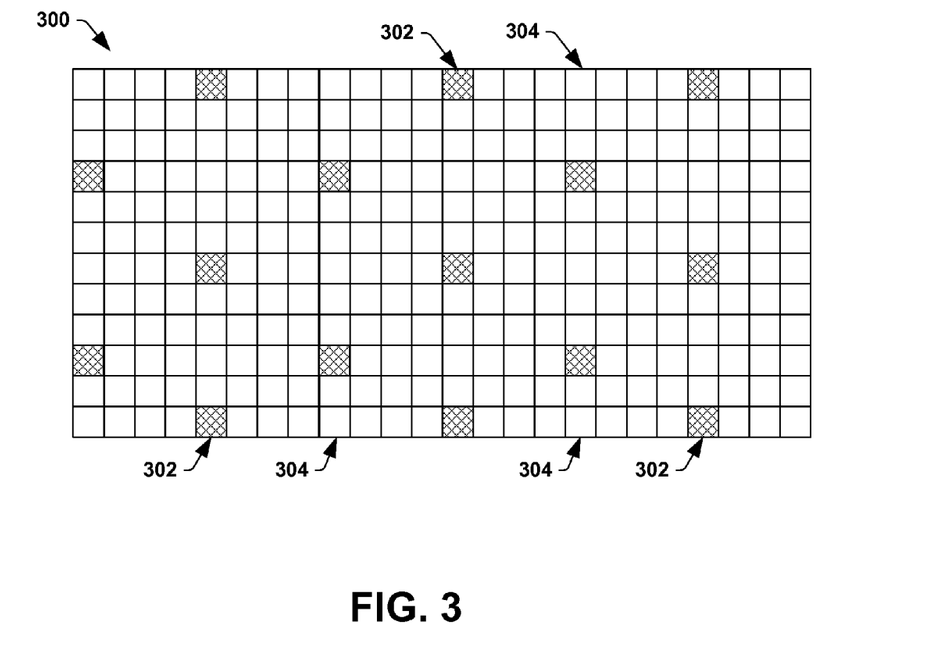
FIG. 3 illustrates an example detector array comprising sparsely arranged energy-resolving detectors.

It will be appreciated that FIG. 2 illustrates merely one embodiment for generating a CT density image (e.g., via a CT scanner 208) and sparse multi-energy projection data (e.g., via a multi-energy line scanner 210). Other systems and/or techniques are also contemplated for generating such data. For example, FIG. 3 illustrates another technique for generating sparse multi-energy projection data. More particularly, FIG. 3 illustrates a top-down view of a CT detector array 300 (e.g., 218 in FIG. 2) that comprises energy-resolving detectors 302 and, single-energy detectors 304. The energy-resolving detectors 302, which are sparsely arranged within the detector array 300 and are represented as being checkered, are configured to discriminate detected radiation having an energy that falls within a first energy spectrum from radiation having an energy that falls within a second energy spectrum (e.g., whereas the single-energy detectors 304 are typically not configured to make such a discrimination). Thus, data generated from the single-energy detectors 304 is typically utilized to merely construct a CT density image(s) whereas the multi-energy detectors 302 may be utilized to acquire the sparse multi-energy projection data. In this way, the CT scanner may be utilized to generate single-energy, volumetric data (e.g., used to generate the CT density image(s)) as well as sparse multi-energy projection data, for example.

Figure 4:
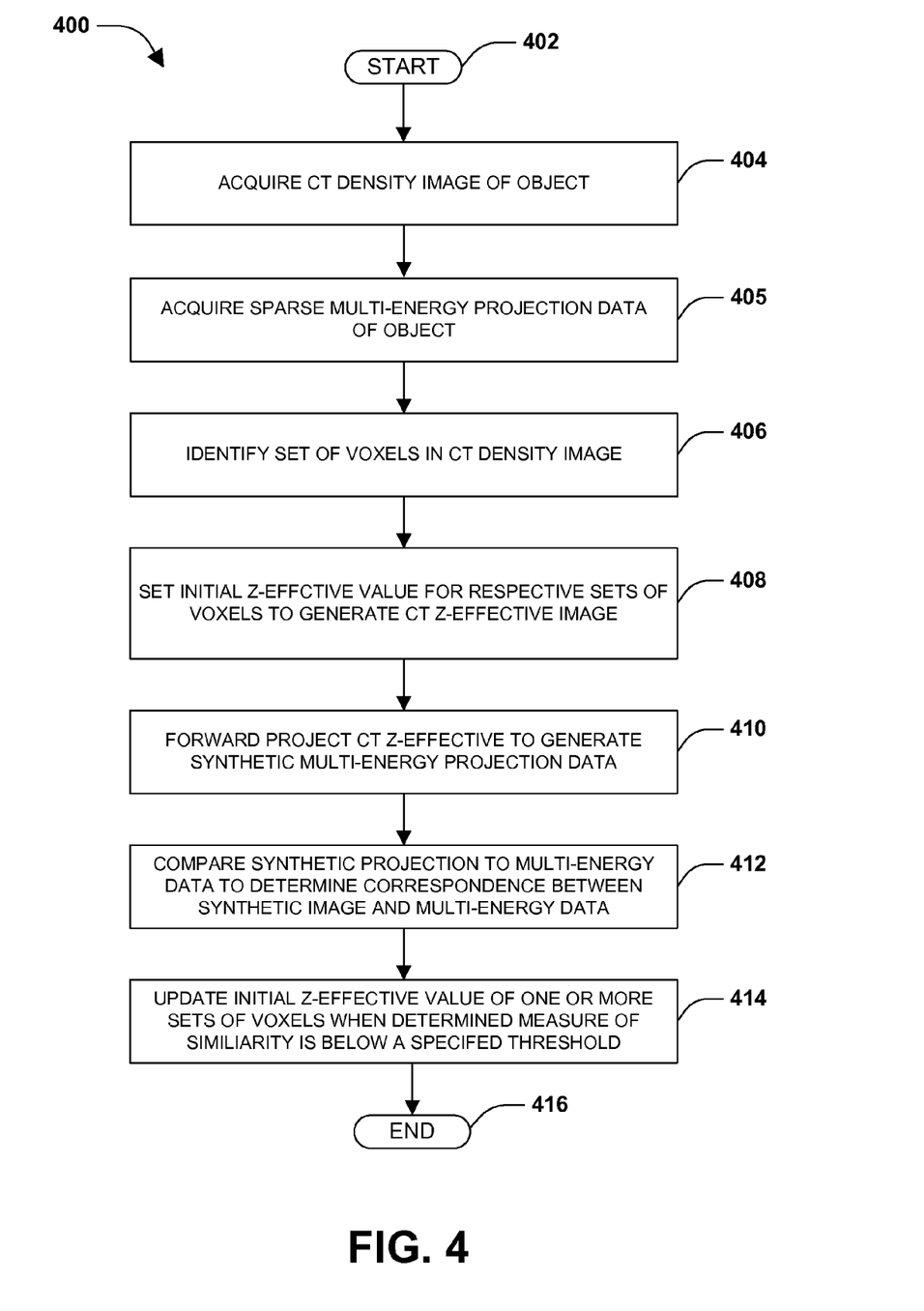
FIG. 4 is a flow diagram illustrating an example method for determining z-effective values for a set of voxels.

FIG. 4 illustrates a flow diagram of an example method 400 which may be utilized (e.g., by a z-effective value generation component 118 in FIG. 1) to generate and/or derive z-effective values for a set of voxels using a CT density image and sparse multi-energy projection data.

The example method 400 begins at 402, and a CT density image of an object under examination is acquired at 404 (e.g., by the z-effective value generation component 118 from the CT image reconstructor 114). As described above, it will be appreciated that while some multi-energy projection data may have been used to construct the CT density image (e.g., if the CT detector comprises energy-resolving elements as illustrated in FIG. 3), merely a CT density image is derived because the amount of multi-energy projection data is insufficient to perform a multi-energy decomposition process and/or to identify z-effective values for respective voxels.

At 405 in the example method 400, sparse multi-energy projection data of the object under examination is acquired. As described above, the sparse multi-energy projection data may be acquired using the same imaging modality as the CT density image and/or may be acquired using a different imaging modality. For example, as described above, the sparse multi-energy projection data may be acquired from a multi-energy line scanner while the CT density image is acquired from a CT imaging modality and/or both the sparse multi-energy projection data and the CT density image may be acquired from the CT imaging modality. Moreover, it will be appreciated that while the example method 400 describes acquiring the CT density image before acquiring the sparse multi-energy projection data, the order may be reversed.

At 406 in the example method 400, one or more sets of voxels comprised in the CT density image are identified. It will be appreciated that as used herein, a set of voxels may include one or more voxels and may be representative of a volume and/or a two-dimensional slice(s). Typically, voxels are separated on a sub-object by sub-object basis and therefore a set of voxels includes all or substantially all of the voxels that represent a sub-object. For example, voxels representative of a first sub-object of the object under examination may be separated from voxels representative of a second sub-object (and identified as a first set of voxels) using one or more object segmentation techniques. That is, stated differently, one or more object segmentation techniques may be performed on the CT density image to identify objects, and voxels associated therewith, depicted in the CT density image and to separate voxels on a sub-object by sub-object basis. As an example, a suitcase under examination may comprise a bottle containing a liquid. When a CT density image of the suitcase is acquired, voxels representative of the bottle may be segmented from voxels representative of the liquid using one or more object segmentation techniques. Voxels representing the bottle may be labeled as a first set of voxels and voxels representing the liquid may be labeled as a second set of voxels.

It will be appreciated that while reference is made to separating voxels on a sub-object by sub-object basis, the degree of separation may differ based upon, among other things, the resolution of the CT density image. By way of example, in another embodiment, where the CT density image has a low resolution (e.g., causing an edge of a first sub-object to be indistinguishable from an edge of a second sub-object), voxels may be separated on a region-by-region basis. In such an embodiment, voxels within a first region (e.g., which may comprise voxels representative of two or more sub-objects) may be separated from voxels within a second region of the CT density image, for example. In another embodiment, where the CT density image has higher resolution, the voxels may be separated to an even finer degree than on a sub-object by sub-object basis. For example, voxels representative of a first portion of a bottle (e.g., a cap or removable portion) may be separated from voxels representative of a remaining portion of the bottle. Thus, the extent to which voxels are separated (e.g., to create/identify one or more sets of voxels) may vary by application and/or may vary based upon the resolution/clarity of the CT density image, for example.

In one embodiment, voxels that cannot be identified as being representative of a defined sub-object in the CT density image and/or voxels that are representative of sub-objects that are not of interest (e.g., such as clothing, which typically has a relatively low density), may be grouped together and labeled as a single set of voxels, for example. By way of example, in an airport environment, a suitcase is often is comprised of a plurality of clothing items that have similar densities and appear diffused in an image generated via a radiology imaging modality (e.g., there are no clear delineations between a first clothing item and a second clothing item). Such objects are often times difficult to individually segment in a CT density image because the edges of respective items of clothing are difficult to define in the image. Thus, in one embodiment, voxels representative of such items may be grouped into a single set of voxels and may be assigned using a single value from a database, for example.

Moreover, it will be appreciated that metal objects often complicate deriving a z-effective value for sets of voxels of interest because metal objects typically absorbed/deflect substantially all of the radiation coming into contact with the metal objects and because the z-effective value of a metal object is typically substantially higher than the z-effective value(s) of materials of interest (e.g., potential threat items). As such, radiation starvation may occur in regions comprising metal objects causing little, if any, useful information regarding the density and/or z-effective of a metal object to be determined. Moreover, where metal objects overlap, it may be difficult to distinguish a first metal object from a second metal object. Thus, voxels that appear to represent metal objects (e.g., appear as bright white spots in the image) may be grouped into a single set of voxels, for example. In this way, projection data, representing the metal objects, and/or its contribution in the iterative process described herein can be reduced.

At 408 in the example method 400, an initial z-effective value for respective sets of voxels is set. Stated differently, for each of the identified sets of voxels, an initial z-effective value is assigned, causing voxels of the set to also be assigned the initial z-effective value. It will be appreciated that this initial value may be virtually any number because it can be refined later, as will be described below. For example, in one embodiment, the initial z-effective value is a default value that is assigned to respective sets of voxel (e.g., causing each set of voxels to be initially assigned the same z-effective value). In another embodiment, the z-effective value is estimated based upon, among other things, a priori information about the sub-object represented by the voxels, such as an known density about the sub-object, geometric information about the sub-object, and/or an environment at least partially surrounding the sub-object (e.g., density information about nearby sub-objects). Moreover, while reference may be made herein to setting the z-effective value for merely one set of voxels, it will be appreciated that a z-effective value may be set for respective sets of voxels. In this way, most, if not all, voxels of the CT density image may be assigned a z-effective value, for example.

Once a z-effective value is assumed/estimated for respective voxels, a CT z-effective image may be generated using initial z-effective values. Given that the CT z-effective image is derived from the CT density image, the CT z-effective image typically has the same dimensionality as the CT density image. Thus, the CT z-effective image can be an image slice (e.g., a 2D image), collection of slices, and/or a 3D image.

At 410 in the example method 400, the CT z-effective image is forwarded projected to generate synthetic multi-energy projection data. It will be appreciated that this synthetic projection is a multi-energy projection and is therefore indicative of z-effective information and, possibly, density information. As such, a traditional density-based forward projection model may not be sufficient for the forward projection. Rather, a model for forward projecting z-effective information, such as a dual-energy X-ray propagation model, for example, may be utilized to forward project the CT z-effective image and generate synthetic multi-energy projection data. In this way, a 3D, CT z-effective image may be converted to a two-dimensional multi-energy projection and/or a 2D, CT z-effect image may be converted to a one-dimensional multi-energy projection, where the z-effective component of voxels along a converted/collapsed dimension are averaged or otherwise combined in the synthetic z-effective projection.

Moreover, in one embodiment (e.g., to perform a comparison as will be described below), the CT z-effective image is forward projected onto a geometry of the multi-energy detectors (e.g., detectors generating the sparse multi-energy projection data). That is, the CT z-effective image is forward projected along a straight line (e.g., for each multi-energy detector), that aligns the synthetic multi-energy projection data with the sparse multi-energy projection data such that a side-by-side comparison of the synthetic multi-energy projection data and the sparse multi-energy projection data may be made at 412 in the example method 400. For example, a 3D, CT z-effective image may be forward projected to generate a 2D synthetic multi-energy projection that corresponds to 2D sparse multi-energy data and/or a 2D z-effective image may be forward projected to generate a 1D synthetic multi-energy projection that corresponds to 1D sparse multi-energy data. It may be appreciated that the synthetic multi-energy projection data is representative of what a measured projection would look like if the z-effective values set at 408 in the example method accurately reflect the effective atomic number(s) of an object under examination, for example.

It will be appreciated that in order to forward project the CT z-effective image onto a geometry of the multi-energy detectors, a geometry of the multi-energy detectors (e.g., a geometry in which the sparse multi-energy projection data was acquired) may be determined using a registration process if not known (precisely) at the time forward projection is carried out. Such a registration process may be configured to determine a spatial orientation of the imaging modality generating the CT density image relative to the imaging modality generating the sparse multi-energy projection data. In this way, a beamline and/or images yielded from a first imaging modality may be defined in a substantially similar coordinate system as the beamline and/or images yielded from second imaging modality, for example. Where the same imaging modality (e.g., a CT imaging modality) is generating both the CT density image and the sparse multi-energy projection data, the relative spatial orientation may be known and such a registration process may not be necessary, for example.

At 412 in the example method 400, the synthetic multi-energy projection data (e.g., generated at 410) is compared to the sparse multi-energy projection data (e.g., acquired at 405) to determine a measure of similarity between z-effective information of the synthetic multi-energy projection data and z-effective information of the sparse multi-energy projection data. That is, the synthetic multi-energy projection data is compared to the sparse multi-energy projection data to determine whether the synthetic multi-energy projection data (e.g., which represents a guess/estimate of z-effective information) matches the sparse multi-energy projection data (e.g., the measured multi-energy projection data). The higher the measure of similarity and/or the closer the match, the better the assumed/estimated z-effective values reflect the effective atomic number(s) of the object because the sparse multi-energy projection data reflects a measured view of such information. Stated differently, a match and/or a high measure of similarity indicates that the assumed/estimated z-effective values are within a reasonable estimation of the z-effective values that would have been obtained from a multi-energy CT apparatus. That is, the further the synthetic multi-energy projection data deviates from the sparse multi-energy projection data, that greater the dissimilarity between the two sets of projection data. When the deviation exceeds a specified threshold, the initial z-effective values for one or more sets of voxels may be updated as described with respect to 414 in the example method 400.

At 414 in the example method 400, the initial z-effective value for one or more sets of voxels is updated based upon the measure of similarity when it is determined that the measure of similarity is below a specified threshold. That is, stated differently, when the measure of similarity is below a specified threshold (e.g., indicating that the assumed/estimated z-effective values do not reflect what would have been the z-effective values derived from a dual-energy CT), the z-effective value for one or more sets of voxels may be updated/refined based upon the comparison. It will be appreciated that numerous iterative technique for determining how to update and/or refine the z-effective value for one or more sets of voxels based upon the comparison are contemplated for use herein. For example, in one embodiment, the update may be based upon energy differences between the synthetic multi-energy projection data and the sparse multi-energy projection data.

It will be appreciated that if the z-effective value of one or more sets of voxels are refined/updated, the CT z-effective image derived therefrom may also be updated to reflect that change in a z-effective value(s) and may be forward projected to generate updated synthetic multi-energy projection data. This updated synthetic multi-energy projection data may be compared to the sparse multi-energy projection data (e.g., the measured multi-energy projection data) to determine whether the update improved upon the measure of similarity. Such an iterative process of refining the z-effective value of one or more sets of voxels, updating the CT z-effective image based upon the changes to the z-effective value of one or more sets of voxel, forward projecting the updated CT z-effective image, and comparing the updated synthetic multi-energy projection data to the sparse multi-energy projection data may be repeated until the measure of similarity is equal to and/or exceeds a specified threshold and/or until the iterative process has reached another stopping threshold (e.g., a specified number of iterations have been completed, time period has timed out, etc.), for example.

Once the iterative process is complete (e.g., the measure of similarity is equal to or above a specified threshold and/or other stopping criteria has been met), the present z-effective values for a set of voxels (e.g., at the time the stopping threshold is met) may be output and/or the CT z-effective image generated at 408 may be output for display. In this way, z-effective values for a set of voxels reflective of an effective atomic number(s) of an object under examination may be determined using a CT density image and sparse multi-energy projection data, for example.

It will be appreciated that in one embodiment, in addition to outputting the z-effective values for a set of voxels, a confidence value may also be calculated and/or output. The confidence value may be a measure of the mismatch between the sparse multi-energy projection data (e.g., the measured multi-energy projection data) and the synthesized multi-energy projection data. Stated different, the confidence value may be indicative of how likely it is that the estimated/derived z-effective values reflect the effective atomic number value(s) of the object under examination (e.g., the confidence measure is an estimate of the confidence in the determined z-effective values for the object). It will be appreciated that numerous metrics may be considered when computing a confidence value. For example, in one embodiment, the confidence value may be a function of, among other things, a percentage of an object surface in the sparse multi-energy projection data that is not indicative of metal sub-objects, the residual energy of the object (e.g., including or excluding the energy of radiation passing through metal sub-object(s)), percentage of metal sub-objects overlapping other sub-objects/aspects, and/or a ratio of the average density of the object relative to the average density of merely background sub-objects (e.g., clothing and/or other diffused items).

The example method 400 ends at 416.

Figure 5:
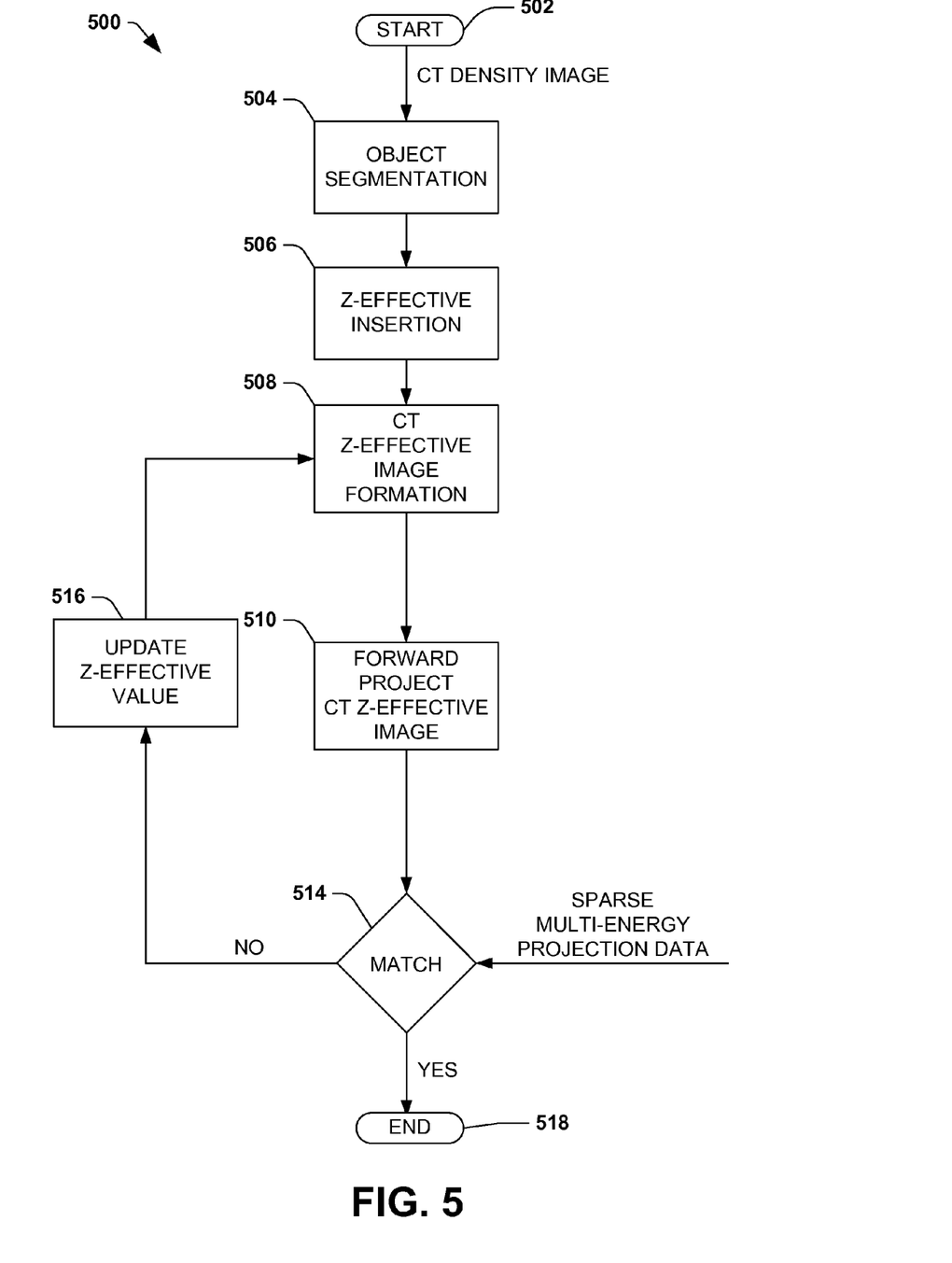
FIG. 5 is a flow diagram illustrating an example method for determining z-effective values for a set of voxels.

FIG. 5 illustrates a flow-diagram of yet another example method 500 for obtaining z-effective values for a set of voxels from a CT density image and sparse multi-energy projection data. Such an example method 500 may be performed by an z-effective value generation component (e.g., 118 in FIG. 1), for example.

The example method 500 begins at 502, where a CT density image is acquired from an examination using a computed tomography scanner and/or other radiology imaging system configured to produce volumetric images. Using the CT density image, object segmentation is performed at 504, whereby sub-objects within the CT density image are separated. More specifically, voxels are divided and grouped according to sub-objects represented thereby (e.g., where a first set/group of voxels is associated with a first sub-object, a second set/group of voxels is associated with a second sub-object, etc.). In this way, in this embodiment, respective sets of voxels are representative of a single sub-object within the CT density image (e.g., although voxels representing two or more sub-objects, such as voxels representing items of clothing, may be grouped together). For example, where the CT density image depicts a bottle comprising a liquid, a first set of voxels may comprise voxels representative of the bottle and a second set of voxels may comprise voxels representative of the liquid within the bottle.

At 506 in the example method 500, respective sets of voxels are assigned a z-effective value. That is, a first z-effective value may be assigned to voxels associated with a first sub-object represented in the image and a second z-effective value may be assigned to voxels associated with a second sub-object represented in the image. The z-effective value assigned to voxels associated with the first sub-object may be the same as the z-effective value assigned to voxels associated with the second sub-object and/or they may differ. Moreover, the z-effective values may be assigned randomly (e.g., without consideration of a priori information) and/or may be assigned/estimated based upon a priori information. For example, objects that have a higher density may, on average, also have a high atomic number. Thus, voxels representing objects that appear to have a higher density may be assigned a greater z-effective value than voxels representing objects that appear to have a lower density.

At 508 in the example method 500, a CT z-effective image is formed based upon the z-effective values assigned to the respective sets of voxels at 506. It will be appreciated that such a z-effective image merely reflects the assumed/estimated values and may not initially be reflective of the effective atomic number(s) of the object under examination. Rather, as described with respect to FIG. 4 and described further below, the z-effective values for respective set of voxels are merely a starting point, and will (presumably) become more reflective of the effective atomic number of the object or sub-objects thereof through successive iterations (e.g., whereby the z-effective value of one or more sets of voxels are adjusted until it is determined that the z-effective values assigned to respective sets of voxels accurately reflect (e.g., within a reasonable tolerance) the effective atomic number(s) of the object under examination and/or until other stopping criteria have been met).

At 510 in the example method 500, the CT z-effective image is forward projected to generate synthetic multi-energy projection data, and this synthetic multi-energy projection data is compared to the sparse multi-energy projection data at 514 (e.g., the measured multi-energy projection data) to determine an accuracy of the assumed/estimated z-effective values. That is (assuming the geometry of the synthetic multi-energy projection data and the sparse multi-energy projection data substantially match), the values of the synthetic multi-energy projection data should substantially match the values of the sparse multi-energy projection data when the assumed/estimated z-effective values substantially correspond to the z-effective of the object (e.g., as reflected in the sparse multi-energy projection data).

If the comparison determines that the synthetic multi-energy projection data does not match the sparse multi-energy projection data (e.g., within a specified amount of deviation), the z-effective value assigned to one or more sets of voxels may be updated at 516 and an updated CT z-effective image (e.g., reflective of the updated z-effective value(s)) may be generated and forward projected to generate updated synthetic multi-energy projection data. Such updated synthetic multi-energy projection data may be compared to the sparse multi-energy projection data to determine whether the update improved the match to achieve a specified measure of similarity. If the measure of similarity is below a specified threshold (e.g., if the updated synthetic multi-energy projection data does not match the sparse multi-energy projection data within a specified degree of deviation), the z-effective value of one or more sets of voxels may be updated again at 516 and the process may be repeated as shown in FIG. 5 until a specified measure of similarity is achieved and/or until some other stopping threshold is met.

Once the specified stopping threshold is met and/or the specified measure of similarity is achieved, the presently determined z-effective values for respective set of voxels may be output for display and/or output for further processing (e.g., via a threat detection component), for example.

The example method 500 ends at 518.

Figure 6:
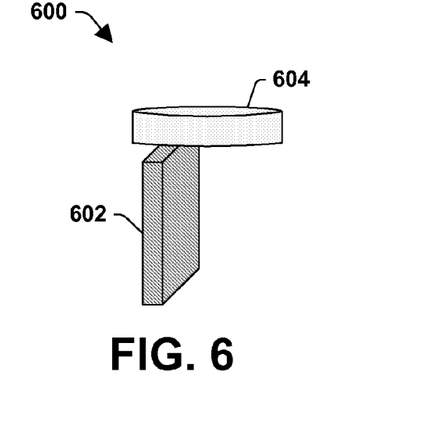
FIG. 6 illustrates an example CT density image.

FIGS. 6-10 provide example illustrations further detailing how a CT density image and sparse multi-energy projection data (e.g., measured multi-energy projection data) may be utilized to generate z-effective values for a set of voxels through an iterative process. More specifically, FIG. 6 illustrates an example CT density image 600 (e.g., a 3D density image), that may be acquired from an examination of a suitcase, for example. It will be appreciated that for ease of understanding, the outline of the suitcase itself has been removed, as has many of the objects that may be comprised in a suitcase (e.g., such as clothing). Thus, the example density image 600 merely illustrates two objects. The first is a square-shaped object 602 having a first density (e.g., as represented by the darker shading) and the second is an oval-shaped object 604 having a second density (e.g., as represented by a different, lighter shading). Although FIGS. 6-10 illustrate the CT density image 600 and CT z-effective image 800 has being 3D, it will be appreciated that in another embodiment, such images may be 2D. Moreover, while the synthetic multi-energy projection data 900 and the sparse multi-energy projection data 1000 are illustrated as being 2D, in another embodiment (e.g., where the CT density image 600 and/or the CT z-effective image 800 are 2D) the synthetic and sparse multi-energy projection data 900, 1000 may be 1D.

Figure 7:
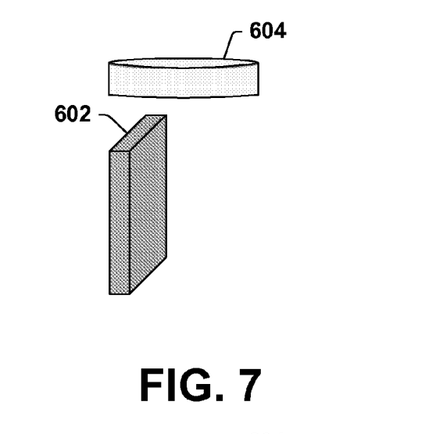
FIG. 7 illustrates an example CT density image after object segmentation.

FIG. 7 illustrates the example objects 602 and 604 after (optional) object segmentation, whereby the first object 602 is disjoined from the second object 604. More particularly, voxels of the CT density image that are associated with the first object 602 are distinguished from voxels that are associated with the second image 604 (e.g., which for purposes of illustration is represented by the separation of the first object 602 from the second object 604).

Figure 8:
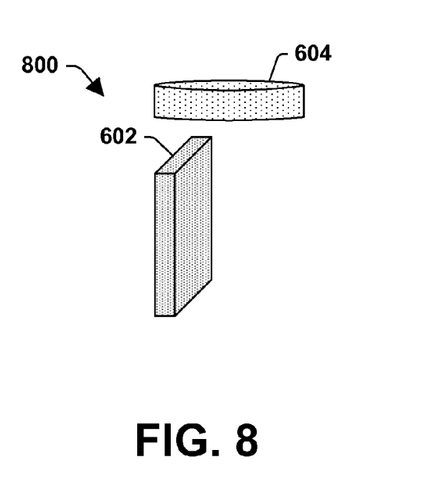
FIG. 8 illustrates an example CT z-effective image.

As described at 508 in the example method 500, a set of voxels representing the first object 602 may be assigned a first z-effective value and a set of voxels representing the second object 604 may be assigned a second z-effective value to generate a CT z-effective image (e.g., having a substantially same, 3D dimensionality as the CT density image 600). FIG. 8 illustrates an example CT z-effective image 800 which may be generated by respectively assigning voxels of the CT density image 600 a z-effective value. In the illustrated CT z-effective image 800, the first object 602 has a first pattern to represent the voxels associated therewith being assigned a first z-effective value. The second object 604 has a second pattern to represent the voxels associated therewith being assigned a second z-effective value.

Figure 9:
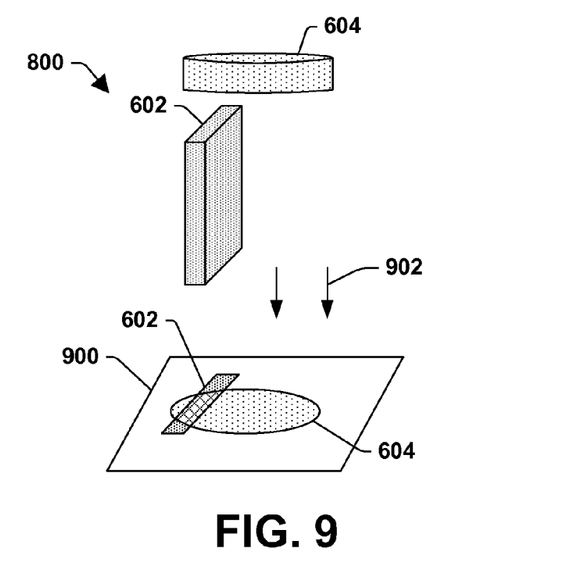
FIG. 9 illustrates an example CT z-effective image being forward projected to generate synthetic multi-energy projection data.
Figure 10:
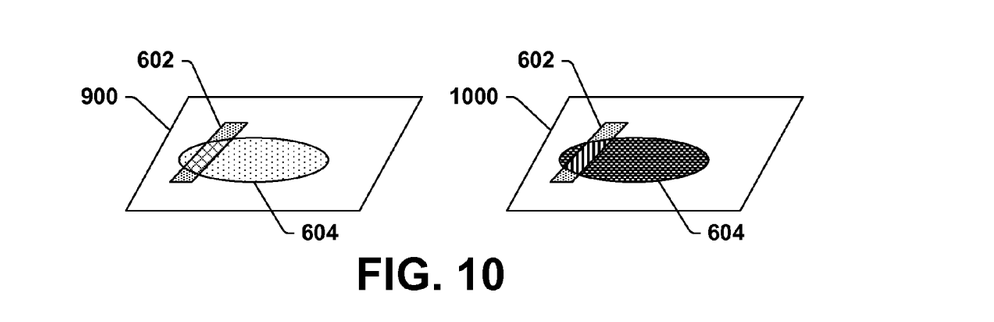
FIG. 10 illustrates synthetic multi-energy projection data being compared to sparse (e.g. measured) multi-energy projection data.

FIG. 9 illustrates the CT z-effective image 800 being forward projected 902 (e.g., onto a geometry of the sparse multi-energy projection data 1000 in FIG. 10) to generate synthetic multi-energy projection data 900. In this way, a 3D, CT z-effective image 800 may be collapsed into a two-dimensional synthetic multi-energy image 900, for example. It will be appreciated that because the image 800 that was forward projected represented z-effective information, the synthetic projection 900 also represents z-effective information. However, given that the two-dimensional synthetic projection 900 lacks the third-dimension of the CT z-effective image 900, the z-effective information of a pixel represents the combination of z-effective information of a plurality of voxels (e.g., stacked in the collapsed dimension).

As illustrated in FIG. 10, the synthetic multi-energy projection data 900 is compared to the sparse multi-energy projection data 1000 (e.g., the measured multi-energy projection data) to determine whether the synthetic multi-energy projection data 900 corresponds to the sparse multi-energy projection data 1000 (e.g., to determine whether the z-effective information of the synthetic multi-energy projection data 900 matches the z-effective information of the sparse multi-energy projection data 1000). As illustrated in FIG. 10, the z-effective information of the square-shaped object 602 in the synthetic multi-energy projection data 900 matches the sparse multi-energy projection data 1000 (e.g., they comprise the same pattern), but the z-effective information of the oval-shaped object 604 in the synthetic multi-energy projection data 900 does not correspond with the z-effective information of the sparse multi-energy projection data 1000 (e.g., they comprise a different pattern). Thus, in such an embodiment, the z-effective value assigned to voxels representing the oval-shaped object 602 may be refined to improve the correspondence of the z-effective information, for example.

Figure 11:
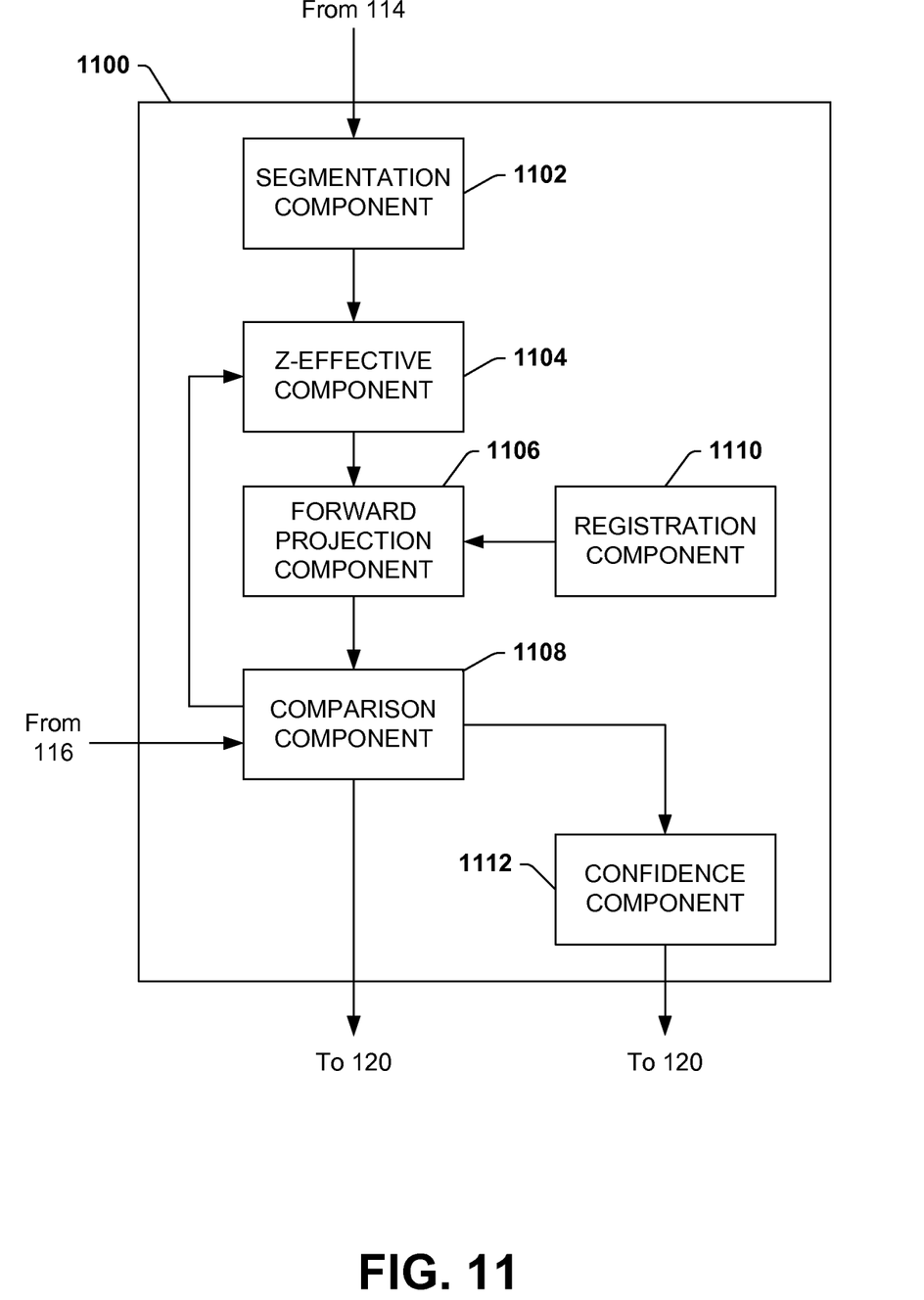
FIG. 11 illustrates a component block diagram of an example system for determining z-effective values for a set of voxels.

FIG. 11 illustrates a component block diagram of an example system 1100 (e.g., 118 in FIG. 1) configured to generate z-effective values for a set of voxels. The example system 1100 comprises a segmentation component 1102 configured to segment one or more sub-objects represented in a CT density image representative of an object under examination using analytical, iterative, and/or other object segmentation techniques. More particularly, the segmentation component 1102 is configured receive a CT density image (e.g., from a CT image reconstructor 114) and group voxels according to sub-objects that are identified in the image such that a first set of voxels, representative of a first sub-object, is separated from a second set of voxels, representative of a second sub-object.

It will be appreciated that objects that are not traditionally segmented from an image may be segmented in accordance with the instant disclosure. However, as provided herein, metal objects may be detected as a superposition of voxels in a predetermined density range and segmented. Moreover, low density (non-threat) items such as clothing may be treated as a single, segmentable object, that is represented by voxels which are not representative of bulk object, sheet objects, and/or metal objects, for example. In this way, most, if not all, of the voxels may be assigned to a group or set of voxels, for example.

The example system 1100 also comprises a z-effective component 1104 configured to set a z-effective value for respective sets of voxels. That is, one or more sets of voxels are respectively assigned a z-effective value. Such an assignment may be random, may be estimated based upon a priori information (e.g., such as density information, geometry information etc.), and/or respective sets of voxels may be assigned a default value. In this way, a CT density image may be transformed into a CT z-effective image (e.g., although the z-effective value assigned to a set of voxels may not necessarily correspond to the actual atomic number of the sub-object represented by the set of voxels).

The example system 1100 also comprises a forward projection component 1106 configured to forward project the CT z-effective image to generate synthetic multi-energy projection data using a multi-energy projection technique, such as a dual-energy propagation model, for example. It will be appreciated that because the synthetic multi-energy projection data merely provides for two-dimensions, the z-effective component of respective pixels of the synthetic multi-energy projection data may be a superposition of the z-effective value for multiple voxels along a collapsed dimension (e.g., a dimension of the z-effective image not included in the synthetic multi-energy projection data). For example, where the synthetic multi-energy projection data is a top-down image, the z-effective value for a pixel representing two or more voxels stacked on top of one another (e.g., looking down on the object from a top of the object) may correspond to a combination of the z-effective values of the two or more voxels.

The example system 1100 also comprises a comparison component 1108 configured to compare the synthetic multi-energy projection data to sparse multi-energy projection data (e.g., measured multi-energy projection data) received from a multi-energy projection scanner (e.g., 112 in FIG. 1) and/or from sparsely arranged energy resolving elements (e.g., 302 in FIG. 3) of a CT detector array (e.g., 300 in FIG. 3), for example. In this way, the comparison component 1108 is configured to determine a measure of similarity between the z-effective information of the synthetic multi-energy projection data and z-effective information of the sparse multi-energy projection data. When the comparison component 1108 determines that a stopping threshold has been reached (e.g., the measured degree of similarity is equal to or exceeds a specified threshold, an amount of change between iterations is below a specified threshold, etc.), the comparison component 1108 may be configured to output the current z-effective values for a set of voxels to a terminal (e.g., 120 in FIG. 1) and/or to other components for further processing (e.g., such as to a threat determiner component), for example.

When the comparison component 1108 determines that the stopping threshold has not be reached (e.g., the measure of similarity in the z-effective information of the synthetic multi-energy projection data and the measured z-effective information of the sparse multi-energy projection data does not rise to a specified threshold), the comparison component 1108 may provide information to the z-effective component 1104 regarding differences in the z-effective information of the synthetic multi-energy projection data relative to the z-effective information of the sparse multi-energy projection data. Based upon this information, the z-effective component 1104 may update and/or modify the z-effective value of one or more sets of voxels to generate an updated CT z-effective image, which the forward projection component 1106 may forward project to generate updated synthetic multi-energy projection data. The comparison component 1108 may then compare the updated synthetic multi-energy projection data to the multi-energy projection data to determine a measure of similarity in the z-effective information and/or to determine if a stopping threshold has been met. Such a process may be repeated until the stopping threshold has been met, and the comparison component 1108 outputs the current z-effective values for a set of voxels, for example.

It will be appreciated that to effectively compare the synthetic multi-energy projection data to the sparse multi-energy projection data, it may be desirable for the geometry of the synthetic multi-energy projection data to substantially match the geometry of the sparse multi-energy projection data. As such, in one embodiment (e.g., where the sparse multi-energy projection data is yielded from a different imaging modality than the CT density image), the example system 1100 may further comprise a registration component 1110 configured to register the geometries of respective imaging modalities and/or to register differences in the geometries of respective imaging modalities using spatial registration techniques. Such a registration may occur once (e.g., during a calibration) and/or may occur numerous times (e.g., such as during the examination of respective objects). Using the registration information acquired by the registration component 1110, the forward projection component 1106 may forward project the CT z-effective image along a geometry that substantially corresponds to the geometry of the sparse multi-energy projection data, for example.

Moreover, in one embodiment, the example system further comprises a confidence component 1112 configured to estimate a confidence of the z-effective values for objects, that are output from the comparison component 1108. More specifically, it will be appreciated that ability to accurately estimate the z-effective values (e.g., atomic numbers) of objects may be influenced by numerous factors. For example, it may be more difficult to accurately estimate the z-effective values of a suitcase that comprises a plurality of large, metal objects (e.g., because a large percentage of the rays are attenuated by the metal objects). Thus, the accuracy of the estimate regarding z-effective values may be less because less information may be available from which to iteratively estimate the z-effective values of objects in the suitcase. In this way, a confidence score may be output by the confidence component 1112 (e.g., for display via a terminal 120) to inform security personal, for example, whether further processing of a piece of luggage may be beneficial to accurately access the security threat of the luggage. For example, when the confidence component 1112 outputs a low confidence score (e.g., indicate that it is more likely that one of more z-effective values for sets of voxels are incorrect), security personal may consider using additional measures to verify that a suitcase is clear of threats.

Figure 12:
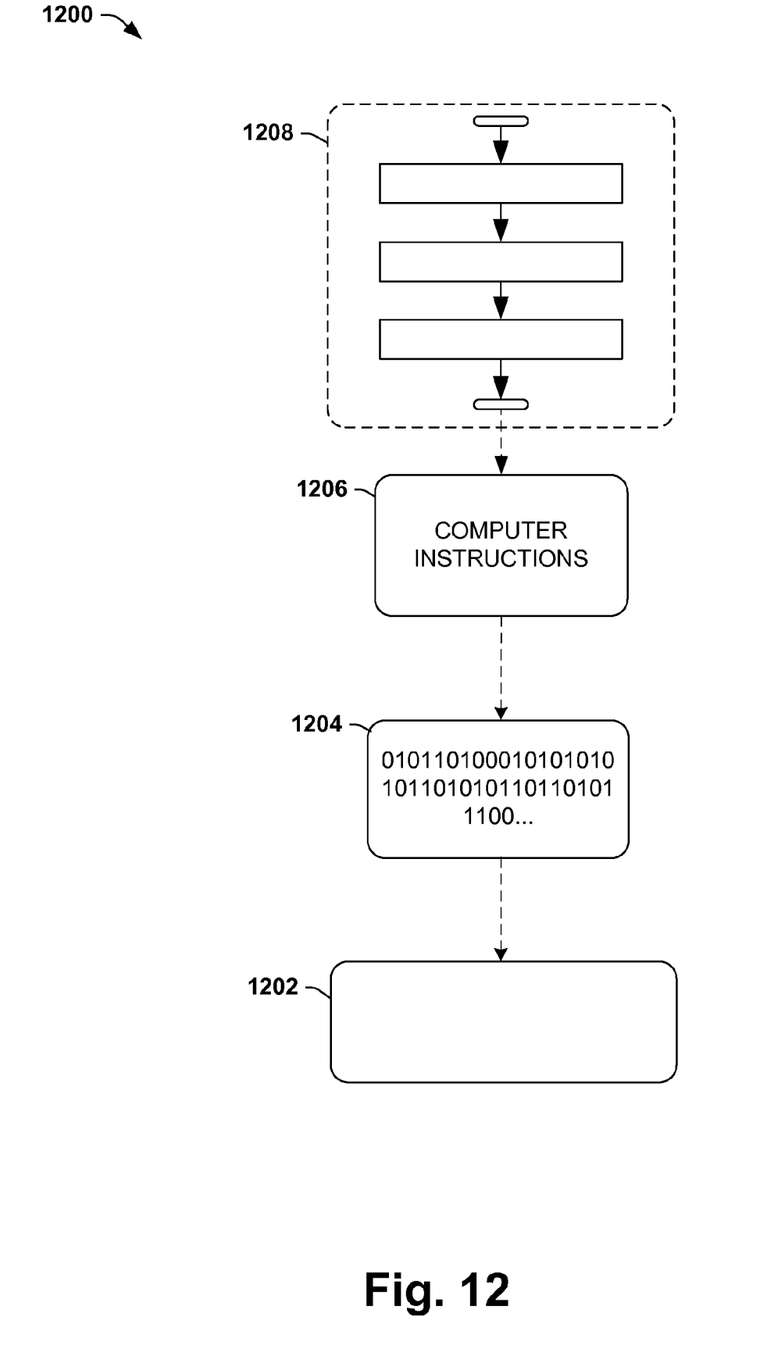
FIG. 12 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 12, wherein the implementation 1200 comprises a computer-readable medium 1202 (e.g., a CD-R, DVD-R, or a platter of a hard disk drive), on which is encoded computer-readable data 1204. This computer-readable data 1204 in turn comprises a set of computer instructions 1206 configured to operate according to one or more of the principles set forth herein. In one such embodiment 1200, the processor-executable instructions 1206 may be configured to perform a method 1208, such as the example method 400 of FIG. 4 and/or 500 of FIG. 5, for example. In another such embodiment, the processor-executable instructions 1206 may be configured to implement a system, such as at least some of the exemplary scanner 100 of FIG. 1 and/or exemplary system 1100 of FIG. 11, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method for generating a z-effective values for a set of voxels in a CT density image for a radiography imaging modality, comprising
    Acquiring the CT density image of an object;
    Acquiring sparse multi-energy projection date of the object;
        Wherein the sparse multi-energy projection data comprising data insufficient for generating a multi-energy image;
    Identifying one or more sets of voxels in the CT density image;
    Setting an initial z-effective value for respective sets of voxels to generate a CT z-effective image;
    Forward projecting the CT z-effective image to generate synthetic multi-energy projection data;
    Comparing the synthetic multi-energy projection data to the sparse multi-energy projection data to determine a measure of similarity between z-effective information of the synthetic multi-energy projection data and z-effective information of the sparse multi-energy projection data; and
    Updating the initial z-effective value for one or more sets of voxels to update the CT z-effective image when the determined measure of similarity between the z-effective information of the synthetic multi-energy projection data and the z-effective information of the sparse multi-energy projection data is below a specific threshold.

2. The method of claim 1, comprising computing a confidence of the determined measure of similarity when the measure of similarity between the synthetic multi-energy projection data and the sparse multi-energy projection data is greater than or equal to a specified threshold.

3. The method of claim 1, forward projecting the CT z-effective image comprising forward projecting the CT z-effective image using a dual-energy X-ray propagation model.

4. The method of claim 1, comprising:
    identifying a first sub-object and a second sub-object in the CT density image; and
    segmenting voxels of the CT density image such that a first identified set of voxels is associated with the first sub-object and a second identified set of voxels is associated with the second sub-object.

5. The method of claim 1, setting the initial z-effective value for respective sets of voxels, comprising setting an initial z-effective value for a first set of voxels based upon a priori information about a sub-object at least partially represented by the first set of voxels.

6. The method of claim 5, the a priori information comprising at least one of density information about the sub-object, geometric information about the sub-object, and an environment at least partially surrounding the sub-object.

7. The method of claim 1, comprising acquiring the sparse multi-energy projection data from a dual-energy line scanner.

8. The method of claim 1, comprising acquiring the sparse multi-energy projection data from a plurality of energy resolving detectors sparsely arranged on a CT detector array.

9. The method of claim 1, comprising, prior to forward projecting the CT z-effective image, determining a geometry in which the sparse multi-energy projection data is acquired.

10. The method of claim 9, forward projecting the CT z-effective image comprising forward projecting the CT z-effective image onto the geometry in which the sparse multi-energy projection data is acquired.

11. The method of claim 1, the sparse multi-energy projection data comprising a two-dimensional projection image.

12. The method of claim 1, the sparse multi-energy projection data comprising data insufficient for generating a multi-energy image.

13. The method of claim 1, comprising:
identifying voxels representative of a metal sub-object in at least one of the CT density image and CT z-effective image; and
discarding the voxels representative of the metal sub-object prior to forward projecting the CT z-effective image.

14. A system for generating a z-effective value for a set of voxels in a CT density image, comprising:
A segmentation component configured to segment one or more sub-objects from the CT density image of an object under examination;
A z-effective component configured to set a first z-effective value for a first set of voxels representing a first segmented sub-object in the CT density image and a second z-effective value for a second set of voxels representing a second segmented sub-object in the CT density image to generate a CT z-effective image;
A forward projection component configured to forward project the CT z-effective image to generate synthetic multi-energy projection data; and
A comparison component configured to compare the synthetic multi-energy projection data to sparse multi-energy projection data indicative of the object to determine a measure of similarity between z-effective information of the synthetic multi-energy projection data and z-effective information of the spars multi-energy projection data,
Wherein the sparse multi-energy projection data comprising data insufficient for generating a multi-enemy image,
Where a measure of similarity that is below a specified threshold is indicative of at least one of the first z-effective value and the second z-effective value differing from an atomic number of a sub-object represented by at least a specific deviation.

15. The system of claim 14, comprising a registration component configured to determine a geometry of an imaging modality generating the sparse multi-energy projection data.

16. The system of claim 15, the forward projection component configured to forward project the CT z-effective image onto the determined geometry such that the synthetic multi-energy projection data and the sparse multi-energy projection data represent substantially similar ray paths.

17. The system of claim 14, comprising a CT imaging modality configured to generate the CT density image and a line scanner configured to generate the sparse multi-energy projection data.

18. The system of claim 14, the z-effective component configured to update at least one of the first z-effective value and the second z-effective value to update the CT z-effective image when the determined measure of similarity is below a specified threshold.

19. The system of claim 14, comprising a confidence component configured to determine a confidence value for the determined measure of similarity, the confidence value indicative of how likely it is that the CT z-effective image represents one or more effective atomic numbers of the object.

20. A non-transitory computer-readable storage medium comprising computer executable instructions that when executed via a processor perform a method comprising:
Setting an initial z-effective value for respective voxels of a CT density image acquired from a single-energy radiography examination of an object to generate a CT z-effective image;
Forward projecting the CT z-effective image to generate synthetic multi-energy projection data; and
Comparing the synthetic multi-energy projection data to sparse multi-energy projection data indicative of the object to determine a measure of similarity between z-effective information of the synthetic multi-energy projection data and the z-effective information of the sparse multi-energy projection data,
Wherein the sparse multi-enemy projection data comprising data insufficient for generating a multi-energy image.

* * * * *